United States Patent [19]
Johnson

[11] Patent Number: 4,575,373
[45] Date of Patent: Mar. 11, 1986

[54] LASER ADJUSTABLE INTRAOCULAR LENS AND METHOD OF ALTERING LENS POWER

[76] Inventor: Don R. Johnson, 9131 Piscataway Rd., Clinton, Md. 20735

[21] Appl. No.: 667,648

[22] Filed: Nov. 2, 1984

[51] Int. Cl.⁴ .............................................. A61F 2/16
[52] U.S. Cl. ..................................................... 623/6
[58] Field of Search .......................... 3/13; 128/303.1; 351/160 R, 176

[56] References Cited

U.S. PATENT DOCUMENTS

| | | | |
|---|---|---|---|
| 4,253,199 | 3/1981 | Banko | 3/13 |
| 4,373,218 | 2/1983 | Schachar | 3/13 |
| 4,461,294 | 7/1984 | Baron | 128/303.1 |

Primary Examiner—Richard J. Apley
Assistant Examiner—James Prizant
Attorney, Agent, or Firm—Allegretti, Newitt, Witcoff & McAndrews, Ltd.

[57] ABSTRACT

A laser beam is utilized to alter, in situ, the power of an implanted intraocular lens. The overall intraocular lens can be of conventional size and shape. The circumference, or outer ring of the lens is manufactured from a non-toxic heat shrinkable plastic. The plastic is preferably colored to permit selective absorption of laser energy thereby causing the shape, and thus the corrective power, of the lens to change. The invention is particularly useful for correcting postoperative astigmatism.

12 Claims, 4 Drawing Figures

LASER ADJUSTABLE INTRAOCULAR LENS AND METHOD OF ALTERING LENS POWER

BACKGROUND OF THE INVENTION

This invention relates to an intraocular lens. In particular, this invention relates to an intraocular lens that can have its prescriptive or refractive power altered while positioned in the eye.

The eye is a complex organ that permits a person to see. In its simplest form, the eye consists of a transparent outer portion called the cornea, a transparent crystalline lens positioned behind the cornea, and the retina, positioned behind the lens. In a normal eye, a person sees when an image passes through the cornea, and that image is in turn focused by the lens onto the retina. The retina then transfers the "image" to the brain.

The crystalline lens in a normal eye is optically transparent. It adjusts its thickness, e.g. focuses, in response to the distance between the eye and the object being viewed. Essential to good vision is the optical transparency or crystallinity of the lens. Advancing age and various diseases can alter the crystalline properites of the lens by the formation of dark spots or opacities known medically as cataracts in the lens. The effect of a cataract on good vision is the same as a dirty window. The cataract interferes with light passing through the lens and impinging on the retina.

The current treatment for cataracts is to surgically remove the lens so that light can once again reach the retina. This is equivalent to removing or washing the previous dirty window. When the lens is removed however, the person loses that part of the eye—the lens—that serves to focus and form sharp images on the retina. Images still form on the retina but they are diffuse, ill-defined and otherwise out of focus.

As a result, when a lens is removed to eliminate cataracts, it must be replaced by an artificial lens. This can be done by providing spectacles to be worn on the face of the patient. Spectacles for patients having the natural eye lens removed (also known as aphakic patients) are quite thick, heavy and unattractive. Contact lenses are an alternative to spectacles since the aphakic patient will not be required to wear heavy, bulky, unattractive spectacles. A disadvantage of contact lenses however is that the typical aphakic patient is a senior citizen who finds it difficult to handle the small contact lens when it is being transferred from its storage container and is being placed in or removed from the eye. As a result senior citizens often lose, damage, or misplace the contact lens.

The most preferred method for restoring vision in an aphakic patient is to surgically implant a lens within the eye. Such a lens, known to ophthalmologists as an intraocular lens, need not and cannot be removed on a regular basis and since it is positioned in approximately the same position as the natural lens, provides vision correction without undue magnification of the image.

A problem associated with the proper implantation of an intraocular lens is the accurate determination of the exact prescriptive or refractive power of the lens to be placed in the patient's eye. The ophthalmologist can, for example, attempt to measure the prescriptive power of the patient's natural lens and, through the use of various measuring devices, e.g. ultrasound, measure the depth and diameter of the eye. These measurements in conjunction with clinical experience permit the opthalmologist to relatively accurately determine the proper refraction or power of the intraocular lens to be placed in the patient's eye. In the vast majority of the cases, the aphakic patient can have an intraocular lens implanted which provides good distance visual acuity even though spectacles will be required for reading since the intraocular lens cannot change its refraction or power like a natural lens.

In some cases however, despite the best efforts of the opthalmologist, the lens surgically placed in the patent's eye does not provide good distance visual acuity. In particular, presently available intraocular lens do not correct astigmatic refractive errors. Since most of the astigmatism present after cataract surgery is due to the surgical incision and changes in corneal curvature attendant to the incision's healing, the exact amount and axis of astigmatism cannot be accurately determined until some time, usually several weeks, after the surgery. Since the old intraocular lens cannot be readily removed and a new intraocular lens with a different power surgically installed without unduly jeopardizing the aphakic patient's vision, the patient must rely on spectacles to provide good distance visual acuity. In other words, although the need to wear heavy, bulky, unsightly spectacles is eliminated, the patient will nevertheless be required to wear spectacles on a full time basis for good distance vision or to cure postoperative astigmatism.

The prior art has recognized this problem. For example, Schachar U.S. Pat. No. 4,373,218 describes an intraocular lens having the form of a fluid expansible, optically transparent sac which can be expanded or contracted by fluid pressure to vary the power of the intraocular lens.

The prior art has also used lasers in conjunction with the correction of vision defects. For example, lasers have been used to repair retinal detachments and to reduce edema in the macula. In addition, as described in U.S. Pat. No. 4,461,294, light absorbing bodies are deposited in preselected portions of the cornea. These light absorbing bodies are then contacted with a laser to generate scar tissue which alter the shape of the cornea thereby correcting refractive errors of the eye.

Lasers have also been used in conjunction with intraocular and contact lenses. For example, lasers have been used to mark plastic lenses as described in U.S. Pat. No. 4,219,721 or to actually machine and polish an optical surface during manufacture of a lens as described in U.S. Pat. No. 4,307,046.

SUMMARY OF THE INVENTION

It is an object of this invention to provide a method of altering the corrective power of an implanted intraocular lens.

It is a specific object of this invention to provide a method of altering the corrective power of an implanted intraocular lens utilizing laser energy.

It is another object of this invention to provide an intraocular lens which can be implanted in an eye and which can have its corrective power effectively and safely altered by contact with laser energy.

In accordance with the present invention, these objects are accomplished by contacting a selected portion of an intraocular lens, while it is implanted in the eye with a laser beam. The intensity of the laser beam and time of contact are selected to provide conditions sufficient to alter the shape of the intraocular lens thereby altering its corrective power without substantially and permanently harming the eye. Preferably the selected portion of the lens is a heat shrinkable plastic colored to permit selective absorption of the laser beam. Particularly preferred is an intraocular lens having a heat shrinkable peripheral or circumferential portion which, when contacted with laser energy is capable of selectively altering the shape and thus the corrective power of the intraocular lens. This heat shrinkable outer portion can be in the form of a concentric ring positioned adjacent to the outer edge of the lens or alternatively, a plurality of discrete, spaced apart sections.

Other objects and embodiments of the present invention are described in the following more detailed description of the present invention.

DETAILED DESCRIPTION OF THE INVENTION

Figure 1:
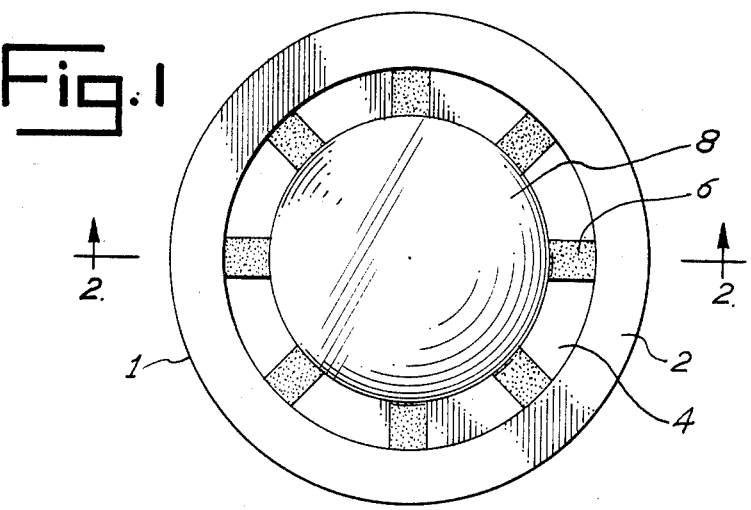
FIG. 1 is a plan view of one embodiment of a laser adjustable intraocular lens.
Figure 2:
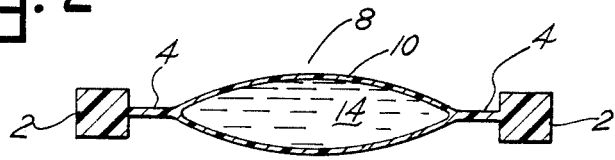
FIG. 2 is a side sectional view of the laser adjustable intraocular lens illustrated in FIG. 1.

Referring in further detail to FIGS. 1 and 2, there is illustrated an intraocular lens 1 formed from a relatively rigid outer ring member 2 interconnected by a continuous heat shrinkable plastic ring 4 to an optically clear lens section 8. The rigid outer ring 2 can be equipped with various attaching members, not shown, sufficient to implant the overall intraocular lens 1 into an eye. For example, various anterior and posterior loops, struts or clasps used in accordance to the various needs and preferences of ophthalmologic surgeons can be used in conjunction with attaching the ring to the interior of the eye. For example, arms and legs such as illustrated in U.S. Pat. No. 4,370,760 may be attached to ring 2 to provide an intraocular lens implant to fit a variety of anterior chamber diameters.

The lens section 8 of intraocular lens 1 comprises a pair of interconnected clear, flexible faces 10 and 12 interconnected at their circumference to provide an enclosed chamber or sac containing an inert optically transparent fluid, gel, or other pliable substance 14. The geometry of this chamber is adjustable and can be in the general form described in U.S. Pat. No. 4,373,218.

The peripheral portions of lens section 8 are attached to outer ring 2 through flat, heat shrinkable plastic ring 4. Ring 4 can be manufactured from any conventional heat shrinkable material that is non-toxic to the eye and will not release toxic substances on heating, such as polyvinyl fluoride (Tedlar), polymethylmethacrylate and Prolene, a polypropylene manufactured by Ethicon, Inc. which will shrink upon application of heat. As illustrated, flat connecting ring 4 is a continuous ring which connects the entire outer circumference of lens section 8 with the entire inner circumference of ring 2. However, it is possible to interconnect ring 2 with lens portion 8 by a plurality of separate and discrete heat shrinkable plastic pieces in the same manner as spokes of a wheel.

Colored portions 6 are spaced around interconnecting ring 4 to provide not only a location to aim or direct the laser beam at but more importantly a location that will more efficiently absorb the laser energy and to create heat only in the portion of the ring upon which the laser is directed. Colored portions 6 are colored with pigments which when contacted with the intensity of the laser beam safely absorb the laser beam and heat the plastic without substantial, permanent damage to the eye. The exact color selected is not critical. For example, red colors approximately the colors of the retina are preferred to use with a ruby laser.

In operation, the corrective power of intraocular lens 1 is altered by focusing the laser on one or more colored portions 6 for time sufficient to cause the heat shrinkable plastic to heat up and thus shrink thereby changing the relationship between flexible faces 10 and 12 of lens section 8. In other words, by shrinking the interconnecting ring 4, the power of the intraocular lens is changed. It should be noted that the ophthalmologic surgeon is capable of predicting relatively accurately the correct power to place in the eye and that the amount of adjustment necessary to obtain good visual acuity is slight. As a result the amount of heat shrinkage required is not substantial so as to minimize the amount and duration of laser energy applied to the intraocular lens thereby avoiding any damage to other portions of the eye.

Figure 3:
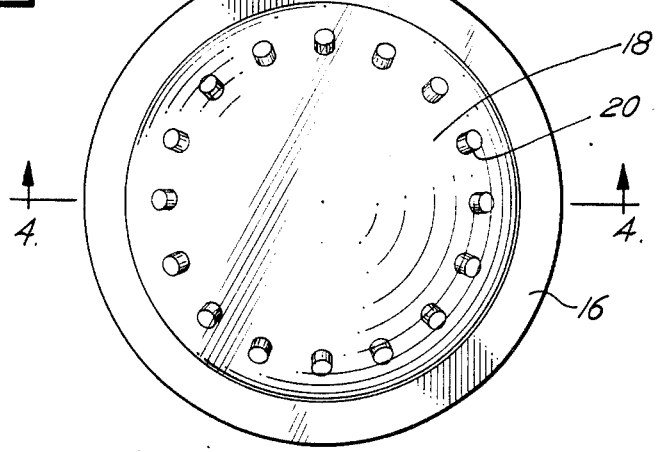
FIG. 3 is a plan view of another embodiment of a laser adjustable intraocular lens.
Figure 4:
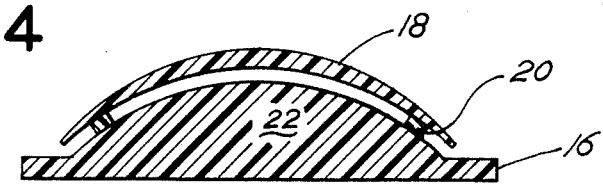
FIG. 4 is a side sectional view of the laser adjustable intraocular lens illustrated in FIG. 3.

Another embodiment utilizing the principles of the present invention is the intraocular lens 19 illustrated in FIGS. 3 and 4. In this embodiment, a conventional intraocular lens 16 of relatively low prescriptive power e.g. +10 diopters, is selected. A secondary lens 18 is then superimposed over and attached to lens 16. Lens 18 is preferably a low power lens much in the shape and configuration of a conventional hard contact lens. Peripheral portions of lens 18 are in turn interconnected to the front face 22 of lens 16 through a plurality of colored heat shrinkable discrete minute plastic pillars. Alternatively, plastic members 20 could take the form of a continuous ring analogous to the continuous ring illustrated in FIGS. 1 and 2.

In the embodiment illustrated in FIGS. 3 and 4, the power of the intraocular lens 19 can be changed by directing the laser at the various colored pillars 20 interconnecting lens 18 to intraocular lens 16. As the heat shrinkable plastic pillars heat up and thus shrink in response to contact with the laser beam, the relationship between lens 18 and optical section 22 changes thereby altering the corrective power of the implanted intraocular lens.

As shown in FIGS. 1 through 4, the intraocular lenses 2 and 19 can be altered while present in the human eye to change its corrective power. The corrective power can be changed not only to compensate for a prescriptive power of the lens but perhaps more importantly to also accommodate astigmatism in the cornea. Symetrical applications of laser energy around the circumference of the intraocular lens would tend to alter the power of the lens while maintaining its sphericity, while asymetrical applications would tend to create a cylindrical component to the lens and correct for astigmatism. The ability to selectively change the corrective power of the lens is particularly useful in removing postoperative astigmatism that cannot be properly corrected during surgery.

The identity, intensity and duration of application of the laser used to adjust the intraocular lens of the present invention is not believed to be critical and can be readily selected by a person of ordinary skill in the art. For example, a $CO_2$ laser is not ideal as it has a tendency to vaporize tissure since its wave length is specifically absorbed by water. Accordingly, since the laser beam must first pass through the cornea and aqueous humor before it contacts the implanted intraocular lens, a $CO_2$ laser is not preferred. On the other hand, the monochromatic red (6943 Å) wavelength from a ruby laser results in less energy absorption through the cornea and aqueous humor and as a result, will produce little, if any, irreparable damage to the peripheral fluids and tissues surrounding the light beam. In addition to the ruby laser, an argon laser (4880 Å and 5154 Å), a YAG laser, an Nd-YAG laser, or a helium-neon laser may also be used. In any event, the particular laser used is to be selected in conjunction with the identity of the pigment used in the colored sections of the intraocular lens to provide efficient, but safe, selective heating and resultant shrinkage of the colored, absorptive sections of the intraocular lens.

I claim as my invention:

1. A method for altering the corrective power of an implanted intraocular lens while positioned in an eye which comprises contacting a selected portion of the implanted lens with a laser beam at an intensity and for a time sufficient to alter the shape of the lens thereby altering its corrective power without substantially and permanently harming the eye.

2. A method for altering the corrective power of an implanted intraocular lens as in claim 1 wherein the selected portion of the implanted lens contacted with the laser beam is colored to permit selective absorption of the laser beam.

3. A method for altering the corrective power of an implanted intraocular lens as in claim 2 wherein the colored selected portion is positioned adjacent to the peripheral portion of the lens.

4. A method for altering the corrective power of an implanted intraocular lens as in claim 3 wherein the colored selective portion is a continuous concentric ring positioned adjacent to the outer edge of the lens.

5. A method for altering the corrective power of an implanted intraocular lens as in claim 3 wherein the colored selected portion is a plurality of discrete equally spaced apart colored sections.

6. A method for altering the corrective power of an implanted intraocular lens as in claim 1 wherein the lens is manufactured at least in part from a transparent, heat shrinkable plastic, said laser beam contacting the heat shrinkable plastic.

7. An intraocular lens for implantation into an eye and capable of having its corrective power altered by a laser when positioned in the eye which comprises an optically clear central portion and a heat shrinkable plastic peripheral portion, said peripheral portion having a colored section to receive laser energy, said colored section, when exposed to laser energy being capable of altering the shape of and thus the corrective power of the intraocular lens.

8. An intraocular lens for implantation into an eye and capable of having its corrective power altered by a laser when positioned in the eye as in claim 7 wherein the colored section is a concentric heat shrinkable ring positioned adjacent to the edge of the lens.

9. An intraocular lens for implantation into an eye and capable of having its corrective power altered by a laser when positioned in the eye as in claim 8 wherein the optically clear center section is a flexible fluid filled chamber, the inner portion of the heat shrinkable ring is attached to the periphery of the fluid filled chamber and the outer portion of the heat shrinkable ring is attached to a rigid ring whereby contraction of the heat shrinkable ring changes the power of the optically clear center section.

10. An intraocular lens for implantation into an eye and capable of having its corrective power altered by a laser when positioned in the eye as in claim 7 wherein the intraocular lens comprises a pair of superimposed interconnected lens, said lens interconnected by the heat shrinkable plastic peripheral portion.

11. An intraocular lens for implantation into an eye and capable of having its corrective power altered by a laser when positioned in the eye as in claim 10 wherein the lenses are interconnected by a heat shrinkable plastic ring.

12. An intraocular lens for implantation into an eye and capable of having its corrective power altered by a laser when positioned in the eye as in claim 10 wherein the lenses are interconnected by a plurality of discrete spaced apart heat shrinkable plastic pillars.

* * * * *